United States Patent [19]

Hellstrom et al.

[11] Patent Number: 5,640,244
[45] Date of Patent: Jun. 17, 1997

[54] METHOD AND APPARATUS FOR ON-LINE DETERMINATION OF FIBER ORIENTATION AND ANISOTROPY IN A NON-WOVEN WEB

[75] Inventors: Ake Arvid Hellstrom, Columbus; Walter Anthony Gregory, Mount Gilead, both of Ohio

[73] Assignee: ABB Industrial Systems, Inc., Columbus, Ohio

[21] Appl. No.: 552,269

[22] Filed: Nov. 2, 1995

[51] Int. Cl.[6] .................... G01N 21/86; G01N 21/47; G01N 33/34
[52] U.S. Cl. ............... 356/429; 356/446; 250/559.16
[58] Field of Search ................... 356/429, 446; 250/559.16

[56] References Cited

U.S. PATENT DOCUMENTS

| T932,008 | 3/1975 | Davis et al. | 250/559.16 X |
|---|---|---|---|
| 4,364,663 | 12/1982 | Gardner et al. | 356/446 X |
| 4,574,634 | 3/1986 | Pappano | 73/597 |
| 4,648,712 | 3/1987 | Brenholdt | 356/73 |
| 4,674,332 | 6/1987 | Pace et al. | 73/597 |
| 4,730,931 | 3/1988 | Watson | 356/429 |
| 4,841,223 | 6/1989 | Baum et al. | 73/159 |
| 4,955,720 | 9/1990 | Blecha et al. | 356/429 |
| 5,025,665 | 6/1991 | Keys, IV et al. | 73/597 |
| 5,394,247 | 2/1995 | Vahey et al. | 356/429 |

FOREIGN PATENT DOCUMENTS

| 0612977 | 8/1994 | European Pat. Off. . |
|---|---|---|
| 3007790 | 9/1980 | Germany . |
| 3413558 | 10/1985 | Germany . |
| 457983 | of 1990 | Japan . |

OTHER PUBLICATIONS

"Evaluation of Some Fibre Orientation Measurements", K. J. Niskanen et al., Journal of Pulp and Paper Science: vol. 15, No. 6, Nov. 1989.

"The Measurement of Fibre Orientation And Its Relation to Directional Strength Properties", D. J. Williams, Appita, Nov., 1970, vol. 24, No. 3, pp. 196–200.

Abstract–"Measurement of Fiber Orientation In Paper", Japanese Publication No. 60–231136, Published Nov. 16, 1985, Applicant: Kanzaki Paper Mfg. Co. Ltd.

Abstract–"Instrument for Measuring Orientation of Fiber Without Contact", Japanese Publication No. 03–015743, Published Jan. 24, 1991, Applicant: Mitsubishi Heavy Ind Ltd.

(List continued on next page.)

*Primary Examiner*—Vincent P. McGraw
*Attorney, Agent, or Firm*—Killworth, Gottman, Hagan & Schaeff, L.L.P.

[57] ABSTRACT

On-line measurement of fiber orientation and anisotropy in a non-woven web of material is performed by directing three light sources toward a sensing region of the web. Reflectively scattered light from each light source is detected by a pair of light sensors positioned on either side of an incidence plane including the beam of incident light. Back scattered light from each light source is also detected by at least one light sensor positioned generally above the sensing region. Preferably two back scattered light sensors are provided for each light source, one common light sensor and one dedicated light sensor. The signals from the light sensors for each of the light sources are combined to generate resultant fiber orientation signals which are used to compute a fiber orientation angle relative to the machine direction and an anisotropy characteristic for the web. The three light sources are modulated and the signals from the light sensors are synchronously demodulated such that light simultaneously incident on the sensing region is electrically separated to correspond to optical paths defined by the three light sources. The resulting signals define points on a generally elliptical polar distribution function of a resultant fiber orientation curve. The curve is approximated by an equation with the measured points being substituted into the equation to form a set of three equations with three unknowns which are then solved to determine the fiber orientation and anisotropy of the web being measured.

22 Claims, 5 Drawing Sheets

OTHER PUBLICATIONS

Abstract–"Estimation of Fiber Orientation of Paper and Device Therefor", Japanese Publication No. 03–045795, published Feb. 27, 1991, Applicant: Sanyo Kokusaku Pulp Co Ltd.

Abstract–"Method and Device for Measuring Fiber Orientation of Paper Sheet", Japanese Publication No. 04–113205, published Apr. 14, 1992, Applicant: Sanyo Kokusaku Pulp Co. Ltd.

"On–Line Fiber Orientation Measuring System for Papers", K. Sakai et al., New Oji Paper Co., Ltd., Japanese Tappi Journal, Mar. 1994, vol. 48, No. 3, p. 52 ff, with translation.

"Method for Measuring Fiber Orientation on Paper Surface", Y. Abe et al, Nippon Paper Industries Co., Japanese Tappi Journal, May 1995, vol. 49, No. 5, p. 71 ff, with partial translation.

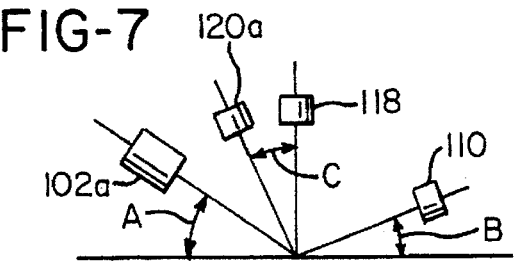
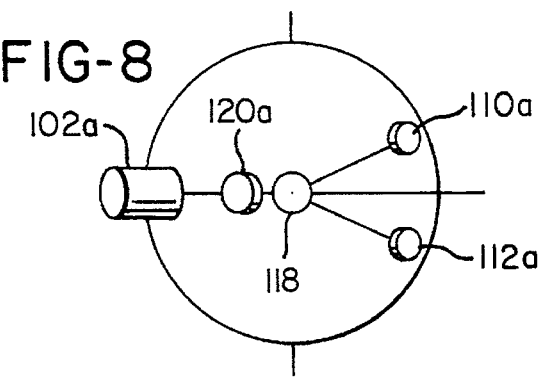
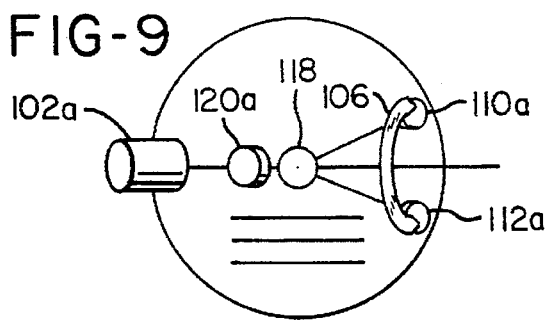
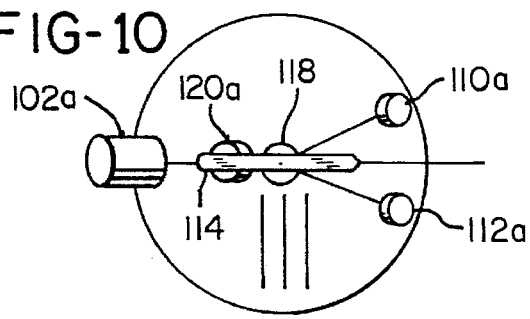

METHOD AND APPARATUS FOR ON-LINE DETERMINATION OF FIBER ORIENTATION AND ANISOTROPY IN A NON-WOVEN WEB

BACKGROUND OF THE INVENTION

The present invention relates in general to on-line measurement of characteristics of webs of material as they are being manufactured and, more particularly, to a method and apparatus for on-line measurement of fiber orientation and anisotropy of non-woven webs of material as they are being manufactured. While the present invention is generally applicable to measurement of a variety of non-woven webs of material, it will be described herein with reference to the manufacture of paper webs for which it is particularly applicable and initially being applied.

Quality requirements for finished paper products continue to increase as the equipment handling such products becomes more and more technologically advanced. For example, modern printing presses and copy machines have significantly increased operating speeds. At the same time, persons using this equipment demand that they operate virtually fault free with no paper breaks, jams, misfeedings or the like. In addition to the higher speed of operation, the possibility for faults is further increased due to the intensive and fast heating and drying of paper for instance in modern copier machines and laser printers.

One characteristic of a paper web which has a large influence on the handling properties of paper produced from the web is the orientation of fibers of the web. A strong orientation in the machine direction dominating over the cross machine direction makes the web stronger in the longitudinal direction but weaker across the web or in the lateral direction. A fiber orientation that has a certain non-zero dominating angle relative to the machine direction commonly occurs due to flow patterns at the wet end of the paper making machine. Such non-zero fiber orientation often causes paper to have diagonal curl, twist, and the like. Of more concern, fiber orientation differences between the top surface and the bottom surface of a web will cause a strong skewing force that will make paper sheets exhibit curl whenever humidity changes. Curl, twist and other deformations due to improper fiber orientation result in problems when handling the paper such that the paper is unacceptable.

Fiber orientation has been measured in the prior art. Fiber orientation measurements are commonly done on finished paper products and thus can only be used to adjust paper making machines prospectively. Such measurements result in the production of substantial amounts of paper webs which may be unacceptable and do not permit control of the paper making machine during production to control fiber orientation. While some fiber orientation measurement techniques have been developed into on-line sensors for measuring one or both sides of a paper web, see for example U.S. Pat. No. 5,394,247 and published European Patent Application 0612977A2, applicant is unaware of any commercially successful on-line sensors which are in operation at this time.

Paper making machines and systems for controlling paper making machines have undergone significant improvements in an attempt to better monitor and control various characteristics of paper webs to thereby produce more and more consistent and higher and higher quality finished paper products. These modern machines provide the ability to dynamically control the quality of the paper web being produced including fiber orientation of the web. Unfortunately, up to this time, on-line measurement of fiber orientation and its control has been lacking.

Thus, there is a need for an economical, accurate on-line measurement for fiber orientation in machines producing non-woven webs of material, such as paper making machines. Preferably, such on-line measurement would measure both fiber orientation of the web and also fiber anisotropy. In addition, the on-line measurement would permit measuring fiber orientation both for the top of the web and for the bottom of the web.

SUMMARY OF THE INVENTION

This need is met by the invention of the present application wherein a method and apparatus are provided for generating signals representative of fiber orientation in a non-woven web of material and, more particularly, for on-line measurement of fiber orientation and anisotropy in a non-woven web of material as the web is being manufactured. While measurements can be made using a single light source, preferably an optical scanner directs at least three light sources toward a sensing region of a web of material being monitored. Light from each light source which is reflectively scattered from the sensing region is detected by a pair of light sensors positioned on either side of an incidence plane including the beam of incident light. Light from each light source which is back scattered is also detected by at least one light sensor positioned generally above the sensing region. Preferably two back scattered light sensors are provided for each light source, one light sensor common to all light sources and one light sensor dedicated to each light source. The signals from the light sensors for each of the light sources are combined to generate resultant fiber orientation signals which are used to compute a fiber orientation angle relative to the machine direction and an anisotropy characteristic for the web.

The multiple light sources are modulated and the signals from the light sensors are synchronously demodulated such that light simultaneously incident on the sensing region is electrically separated to correspond to optical paths defined by the light sources. The resulting signals define points on a generally elliptical polar distribution function of a resultant fiber orientation curve. The curve is approximated by an equation with the measured points being substituted into the equation to form a set of equations, for example three equations with three unknowns, which are then solved to determine the fiber orientation and anisotropy of the web being measured.

In accordance with one aspect of the present invention, a method for on-line measurement of fiber orientation in a non-woven web of material traveling in a machine direction comprises the steps of: directing light from at least three light sources toward a sensing region of the web of material, the light sources being angularly separated from one another and located within a corresponding number of incidence planes which are oriented generally perpendicular to the web of material and intersect at the sensing region for directing light toward the sensing region at incident acute angles relative to the web of material along corresponding axes within the incidence planes; sensing light reflectively scattered from the sensing region at locations approximately diametrically opposite to each of the light sources but on either side of the incidence planes; generating reflectance signals from sensed reflectively scattered light; sensing light back scattered from the sensing region at locations associated with each of the light sources, the back scattered light sensing locations being generally within the incidence planes and positioned above the sensing region; generating back scatter signals from sensed back scattered light; combining the reflectance signals and the back scatter signals for each of the light sources to generate resultant fiber orientation signals; and, computing a fiber orientation angle relative to the machine direction from the resultant fiber orientation signals. Preferably, the reflectively scattered light is filtered using polarizing filters prior to performing the step of sensing the reflectively scattered light received from the sensing region.

The method may further comprise the step of modulating the at least three light sources; the step of generating reflectance signals comprising the step of demodulating sensed reflectively scattered light; and, the step of generating back scatter signals comprising the step of demodulating sensed back scattered light. The method may further comprise the step of computing an anisotropy characteristic for the web of material from the resultant fiber orientation signals. The method may still further comprise the step of angularly separating the light sources from one another by angles approximately equal to 360° divided by the number of light sources.

Preferably, the step of sensing light reflectively scattered from the sensing region comprises the steps of: sensing light a selected number of degrees to the left of each incidence plane and generally diametrically opposite to each of the light sources; and, sensing light a selected number of degrees to the right of each incidence plane and generally diametrically opposite to each of the light sources. For this embodiment, the step of generating reflectance signals from sensed reflectively scattered light comprises the steps of: generating a first reflectance signal from reflectively scattered light sensed a selected number of degrees to the left of each incidence plane and generally diametrically opposite to each of the light sources; and, generating a second reflectance signal from reflectively scattered light sensed a selected number of degrees to the right of each incidence plane and generally diametrically opposite to each of the light sources.

Further, in this embodiment the step of sensing light reflectively scattered from the sensing region is performed at reflective acute angles which are substantially the same as or less than the incident acute angles relative to the web of material. In addition, the step of sensing light back scattered from the sensing region at locations associated with each of the light sources comprises the steps of: sensing light substantially directly above the sensing region; and, sensing light above the sensing region and a selected number of degrees toward each of the light sources generally within the incidence planes. For processing purposes, the step of generating back scatter signals from sensed back scattered light preferably comprises the steps of: generating a first back scatter signal from back scattered light sensed directly above the sensing region; and, generating a second back scatter signal from back scattered light sensed above the sensing region and a selected number of degrees toward each of the light sources generally within the incidence planes.

The step of combining the reflectance signals and the back scatter signals for each of the light sources to generate resultant fiber orientation signals may comprise the steps of: multiplying the first and second reflectance signals by one another; multiplying the first and second back scatter signals by one another; and, dividing the product of the first and second reflectance signals by the product of the first and second back scatter signals. Further, the steps of computing a fiber orientation angle relative to the machine direction from the resultant fiber orientation signals and computing an anisotropy characteristic for the web of material may comprise the step of: solving the equation $R(\alpha)=K/(a+\cos(2(\alpha-\theta)))$ for $\theta$ and $a$ where $R(\alpha)$ is a polar distribution function of the resultant fiber orientation signals, $\alpha$ is a polar coordinate angle and K is a magnitude scaling constant, $\theta$ being a tilt angle of a main axis of orientation of the polar distribution function $R(\alpha)$ representative of the fiber orientation angle, and a being an ellipticity magnitude constant representative of anisotropy of the web.

In accordance with another aspect of the present invention, an optical scanner for determining characteristics of a web of non-woven material comprises at least three light sources arranged to direct light toward a sensing region of the web of material at an acute angle relative to the web of material. The light sources are spaced from one another around the sensing region and direct light along corresponding axes. Pairs of reflective scattered light sensors corresponding in number to the number of light sources are provided with each pair of light sensors being positioned on either side of and spaced from an incidence plane generally perpendicular to the web and including an axis along which light is directed to the sensing region by each of the light sources. The pairs of light sensors generate first sensed light signals in response to received reflectively scattered light, and at least one back scattered light sensor positioned above the sensing region of the web generates second sensed light signals in response to received back scattered light. Preferably, the optical scanner further comprises polarizing light filters associated with the pairs of reflective scattered light sensors for filtering light reflectively scattered from the sensing region.

For signal processing purposes, the optical scanner may further comprise a modulator circuit for generating modulation signals for the light sources. Synchronous detector circuits are coupled to the pairs of reflective scattered light sensors and the back scattered light sensor and are driven by the modulation signals for extracting source signals corresponding to the light sources from the first and second sensed light signals. The modulator circuit may comprise a clock for generating a first signal having a substantially fixed frequency, a first divider circuit for dividing the first signal by 2 to generate a second signal having a frequency substantially half of the first signal, and a second divider circuit for dividing the second signal by 2 to generate a third signal having a frequency substantially half of the second signal. The first, second and third signals then serve as the modulation signals. In a working embodiment of the invention, the first frequency is approximately 40 kilohertz, the second frequency is approximately 20 kilohertz and the third frequency is approximately 10 kilohertz.

The optical scanner may further comprise low pass filters for converting the source signals to reflectance signals representative of the sensed reflectively scattered light and back scatter signals representative of the sensed back scattered light. In a working embodiment of the invention, the low pass filters pass frequencies equal to and below approximately 1 kilohertz.

It is, thus, an object of the present invention to provide an improved method and apparatus for measuring signals representative of fiber orientation of a web of material using reflectively scattered light sensed on either side of an incidence plane including a light source directed at an acute angle relative to the web; to provide an improved method and apparatus for measuring fiber orientation of a web of material while the web is being manufactured, i.e., on-line using reflectively scattered light and back scattered light; and, to provide an improved method and apparatus for measuring fiber orientation of a web of material while the web is being manufactured by directing at least three light sources at the web, measuring reflectively scattered and back scattered light and combining the resulting signals to determine fiber orientation and anisotropy of the web.

Other objects and advantages of the invention will be apparent from the following description, the accompanying drawings and the appended claims.

BRIEF DESCRIPTION OF THE DRAWINGS

FIGS. 7–10 schematically illustrate one light source and associated light sensors for sensing its illumination of a sensing region of a web of non-woven material.

DETAILED DESCRIPTION OF THE INVENTION

The invention of the present application will now be described with reference to the drawings. For clarification of the present invention, its development will first be described. As an initial step, applicant took gloss measurements in the machine direction (MD) and the cross machine direction (CD). The gloss measurements were reflective or specular and resulted in very small differences between the MD measurements and the CD measurements, differences on the order of a few percent. An additional problem in using gloss measurements was detected in that calendering of the paper web during its manufacture would change the results of the test. Thus, a straight forward reflective measurement of a paper web was ineffective for measuring fiber orientation.

Figure 1:
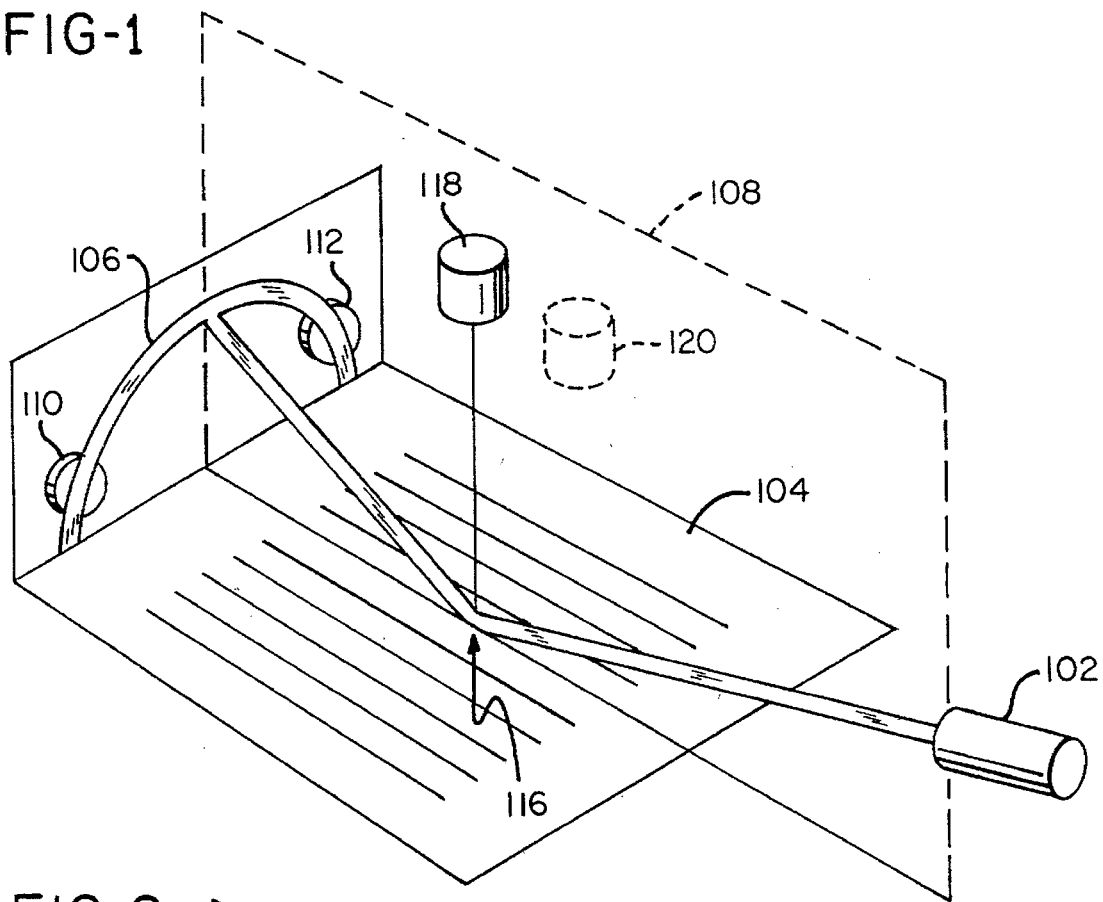
FIG. 1 is a schematic perspective view illustrating light reflectively scattered from a lined surface.

After these initial tests, applicant began considering how to eliminate the insensitivities and fluctuations which resulted when using gloss measurements to detect fiber orientation. Light incident upon a lined surface, for example a metal surface with fine grained parallel grooves made by sanding, grinding, milling or the like, was investigated resulting in the observation that light from a source 102 incident upon a lined surface 104 and paralled to lines of the lined surface 104 produces a reflective scattering of the light with a cone-shaped light distribution 106, as shown in FIG. 1. Reflectively scattered light within the cone-shaped light distribution 106 can be measured off axis, i.e., off the axis of the light source 102 or on either side of an incidence plane 108 of the light source 102, for example by light detectors 110, 112, such that specular changes in the lined surface 104 do not substantially impact the magnitude of the reflectively scattered light.

When light from the source 102 is directed substantially perpendicular to the lines of the lined surface 104, a back scattering of the light with a light distribution 114 substantially within the incidence plane 108 of the light source 102 is produced. Back scattered light within the light distribution 114 can be measured at a location substantially above an illuminated or sensing region 116 of the lined surface 104, for example by at least one light detector 118.

To null out first order disturbances, applicant desired to operate the fiber orientation sensor of the present application in a ratio metric fashion. Accordingly, the ratio of reflectively scattered light signals to back scattered light signals was selected for fiber orientation sensing. Taking the ratio of these two signals produces a much larger differentiation of fiber orientation than using only one signal in view of the characteristics of these signals, i.e., the reflectively scattered light signals are maximum when the back scattered light signals are minimum (for a sample with fiber orientation in line with the measurement path); and, the reflectively scattered light signals are minimum when the back scattered light signals are maximum (for a sample with fiber orientation substantially perpendicular to the measurement path), see FIG. 4. Ratio metric also common mode rejects undesired effects from sheet brightness, source intensity and the like.

Figure 3:
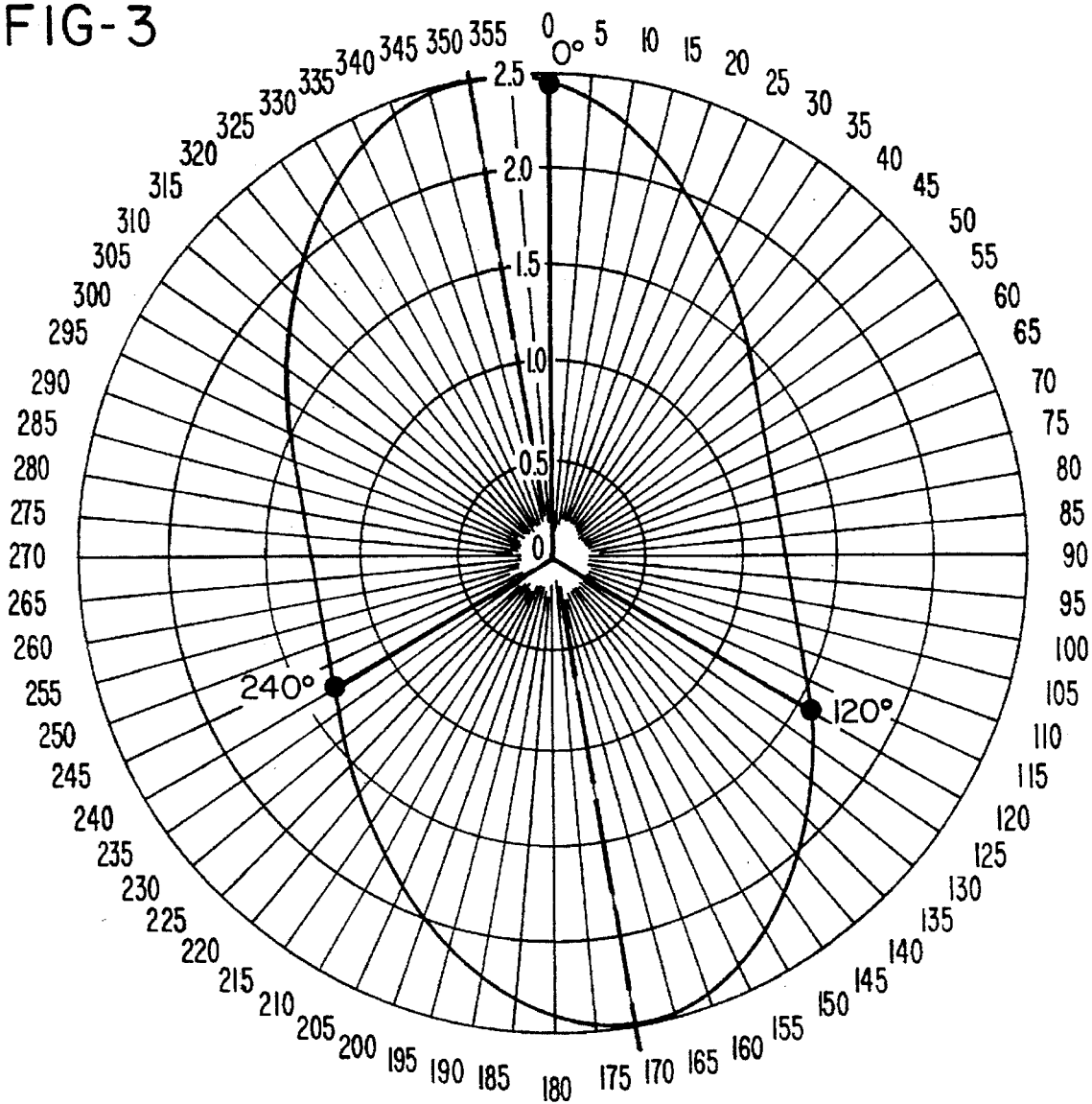
FIG. 3 is an elliptical or semi-elliptical polar ratio distribution of a resultant fiber orientation signal.

A laboratory evaluation was initially performed with a paper sample being turned in a manner similar to the prior art off-line fiber orientation sensing arrangements. Readings were taken every 15° for a full 360° rotation and resulted in a quite pronounced and orientation dependent elliptical or semi-elliptical polar ratio distribution as shown in FIG. 3. Best results have been achieved using a 780 nm IR laser, polarized parallel to the paper surface, as the light source 102, with polarizing filters having a polarizing plane also parallel to the paper surface placed in front of each of the reflectively scattered light detectors 110, 112.

Figure 2:
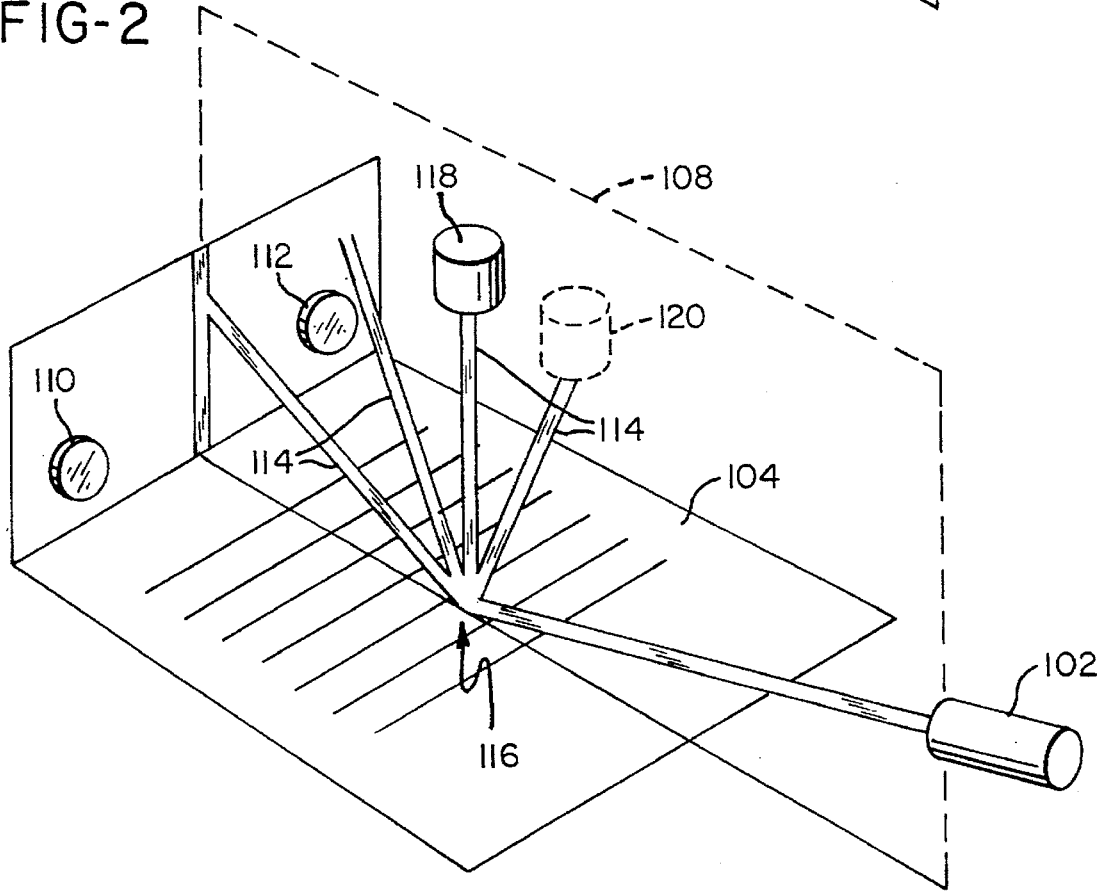
FIG. 2 is a schematic perspective view illustrating light back scattered from a lined surface.

A review of FIGS. 1 and 2 shows that the scattered light patterns change from the conical light pattern of the cone-shaped light distribution 106 if the fiber orientation is parallel to the plane of incidence 108 to a vertical band of the light distribution 114 as the fiber orientation is rotated or shifted to be perpendicular to the plane of incidence 108. As generally illustrated in FIGS. 1 and 2, two light detectors 110, 112 are provided for sensing reflectively scattered light and one light detector 118 is provided for sensing back scattered light. However, to provide symmetry in the signal processing and further enhanced sensitivity, a second back scatter detector 120 can be added as illustrated in dotted lines in FIGS. 1 and 2.

Figure 4:
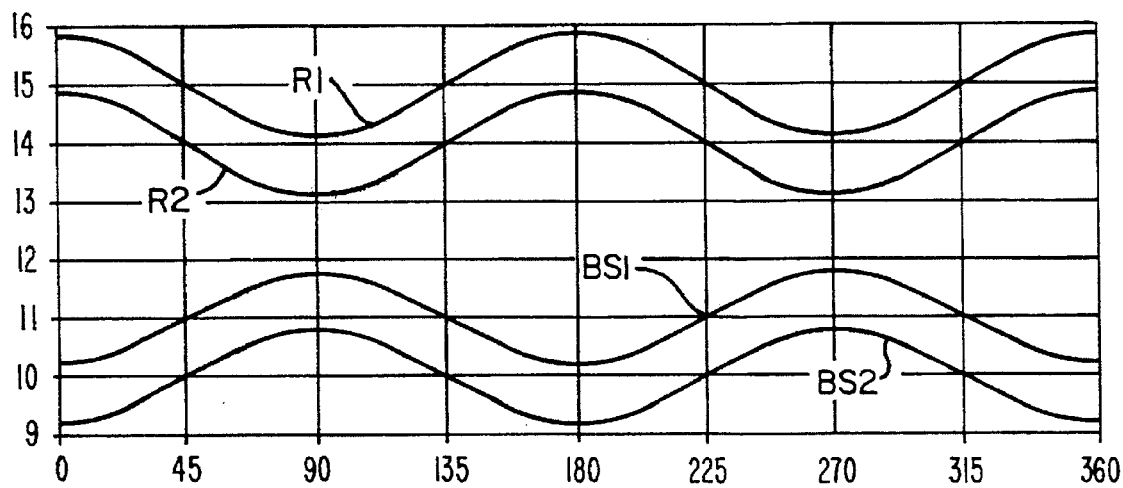
FIG. 4 is an idealized graph of reflectively scattered signals and back scattered signals from an analysis of a portion of a non-woven web of material.

The signals from the light detectors 110, 112, which monitor the reflectively scattered light from the light source 102, and the light detectors 118, 120, which monitor the back scattered light from the light source 102, are processed to solve for a fiber orientation signal R. The resultant fiber orientation signal R is calculated using the equation:

$$R = (R1 * R2)/(BS1 * BS2) \tag{1}$$

where R1 and R2 are the reflectance signals generated by the light detectors 110, 112 and BS1 and BS2 are the back scatter signals generated by the light detectors 118, 120. Idealized graphs of the signals R1, R2, BS1 and BS2 which resulted from the above noted laboratory evaluation are shown in FIG. 4. It is noted that the graphs of FIG. 4 show in principle the signal variations observed during sheet rotation in laboratory experiments, however, the graphs are not of the raw data but have been revised to eliminate noise and irregularities to provide a better understanding of signal generation in the present application.

Continuing from the preceding development outline, the method and apparatus of the invention of the present application for on-line determination of fiber orientation and anisotropy of a non-woven web, such as a paper web, will now be described. As previously noted, if a paper sensor and the light source/light detector apparatus of FIGS. 1 and 2 are rotated relative to one another and readings are taken for a full 360° rotation, an orientation dependent elliptical or semi-elliptical polar ratio distribution as shown in FIG. 3 results.

An ellipse equation is an approximation only valid for small deviations from a circular shape. There are many known methods to mathematically describe oval shapes including multiple trigonometric terms and correction factors for asymmetrical shapes. The choice of a suitable mathematical model for use in an on-line sensor must be sufficiently simple to permit real time processing and yet be accurate over typical ranges of paper products. The applicant of the present application fitted experimental data to several possible equations and decided upon a reasonably good and simple model that is well known in the literature and can be written as:

$$R(\alpha)=K/(a+\cos(2(\alpha-\theta))) \qquad (2)$$

where $R(\alpha)$ is the polar distribution function of the resultant fiber orientation signal, $\alpha$ is the polar coordinate angle, $\theta$ is the tilt angle of the main axis of the fiber orientation, K is a magnitude scaling constant and a ($>1$) is an ellipticity magnitude constant which is representative of fiber anisotropy. The ellipticity magnitude constant is greater for a more circular distribution and lesser for a highly oriented elliptical distribution.

In accordance with the present invention, a set of equations is developed by measuring the resultant fiber orientation signals at a corresponding number of polar angles from 0° to 360°. The measured signals are substituted into equation (2) to form the set of equations which are then solved to measure fiber orientation tilt angle and anisotropy of a web of material as it is being manufactured, i.e., on-line. That is, an unknown distribution function of a resultant fiber orientation signal $R(\alpha)$ is determined, or rather K, a and $\alpha$ are determined, by solving a set of at least three equations resulting from at least 3 given polar measurements at particular angles. In the illustrated embodiment, the 3 defined polar angles are 0°, 120° and 240° as is illustrated in FIG. 3. Three discrete measurements at these angles are used to fully define the polar distribution function $R(\alpha)$, and thereby measure fiber orientation tilt angle $\theta$ and anisotropy a.

In order to measure fiber orientation and anisotropy on-line, it is necessary to perform the measurements without mechanical rotation of either sensor apparatus or the web being measured. To this end, an optical scanner was developed which takes simultaneously three measurements of the web from three different angles. Of course more than three measurements could be taken in accordance with the present invention; however, for cost and complexity considerations, three measurements are currently preferred.

Figure 5:
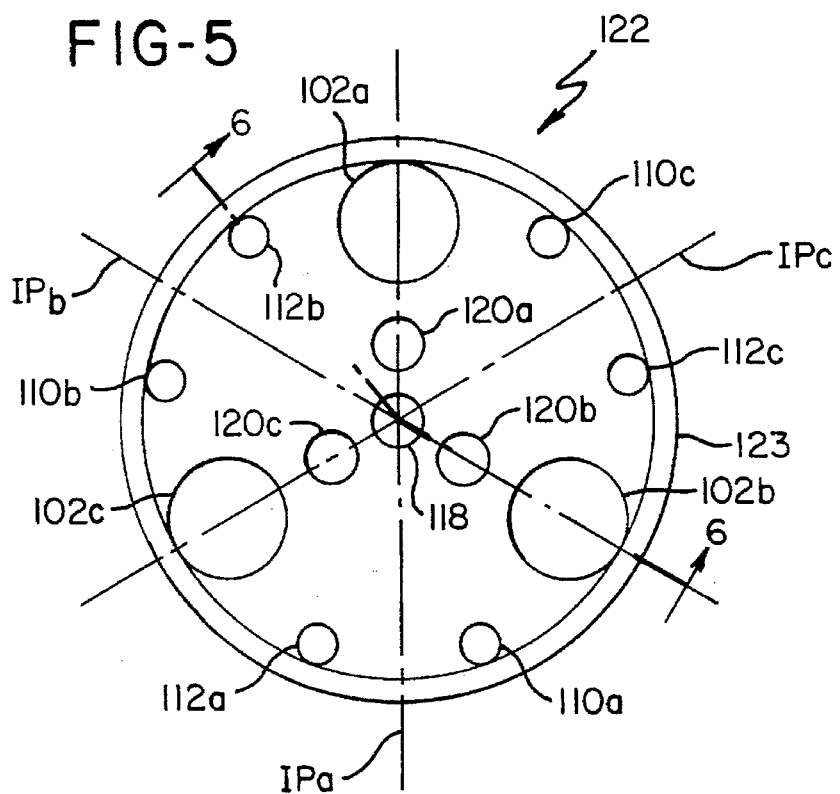
FIG. 5 is a schematic bottom view of an optical scanner in accordance with the present invention.
Figure 6:
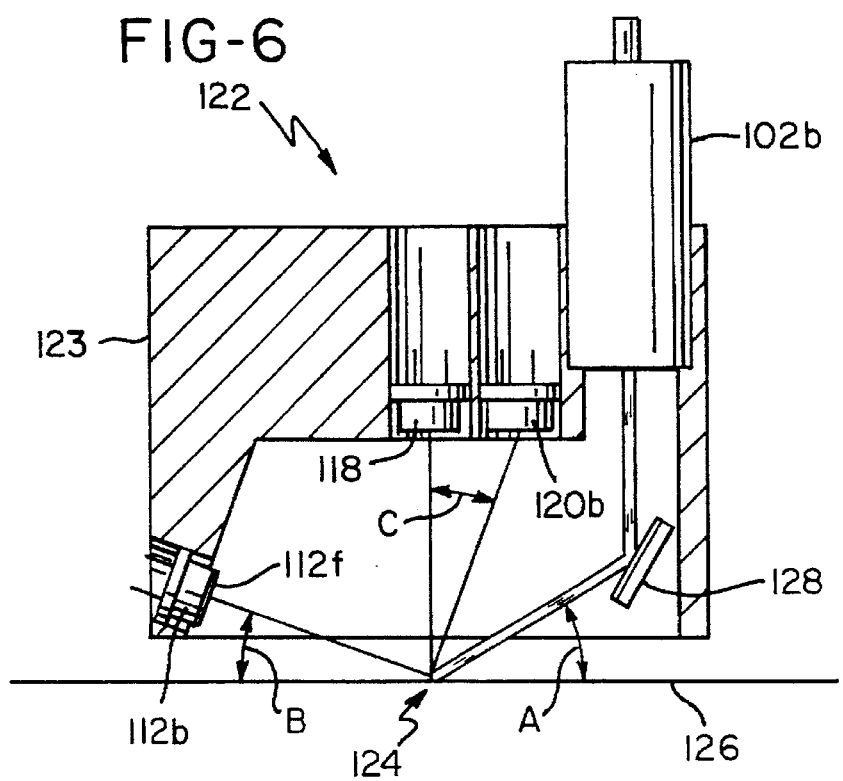
FIG. 6 is a schematic sectional view of the optical scanner of FIG. 5 taken along the section line 6—6.

An illustrative embodiment of an optical scanner 122 with an array of sources and detectors in a circular housing 123 is shown in FIGS. 5 and 6. For this embodiment, light is generated by three sources 102a, 102b, 102c, currently 780 nm IR lasers are the preferred light sources, in a circular symmetrical arrangement spaced at 120° to illuminate a sensing region 124 of a web of material 126 moving through a paper making machine as it is being manufactured. As shown in FIGS. 5 and 6, the light sources are mounted vertically and mirrors, represented by a mirror 128, direct light to the sensing region 124 at an acute angle A.

Three sets of corresponding reflective scattered light sensors 110a–110c and 112a–112c are provided. Due to the cone-shape of the light distribution 106, the reflective light sensors 110a–110c and 112a–112c are arranged to receive light from the sensing region 124 at an angle B which is somewhat less than the angle A. As previously mentioned and as is currently preferred, polarized light sources and corresponding polarizing light filters can be used in front of each of the reflectively scattered light detectors 110, 112. An example of such a polarizing light filter 112f is illustrated in FIG. 6. Although not explicitly illustrated, it should be apparent that polarizing filters can be fitted to or otherwise associated with each of the reflectively scattered light detectors 110, 112.

At least one back scattered light sensor 118 is provided and, preferably, three sets of corresponding back scatter light sensors 118, 120a–120c as will be described, are provided. The central back scattered light sensor 118 is shared for all three light sources 102a, 102b, 102c. As illustrated, the back scattered light sensors 120a–120c are within incidence planes IPa, IPb, IPc of their corresponding light sources 102a, 102b, 102c, and positioned a selected number of degrees C toward each of the light sources 102a, 102b, 102c from the central back scattered light sensor 118, see FIGS. 6 and 7.

To clarify the structure of the optical scanner 122, one light source 102a and light sensors for sensing its illumination of the sensing region 124 are illustrated in schematic form in FIGS. 7–10.

The sensing region 124 is simultaneously illuminated by all of the light sources 102a, 102b, 102c. Accordingly, the individual illuminations caused by each of the light sources 102a, 102b, 102c need to be isolated from one another to solve for the fiber orientation and anisotropy as described above with reference to equation (2). Such signal separation is necessary to measure continuously and at sufficiently high speed that light along all three optical paths within the incidence planes IPa, IPb, IPc can be measured simultaneously. The measurements are to be performed at very high speed with response of the sensors being 1 millisecond or less. In accordance with the invention of the present application, a novel signal processing system 130 has been developed to isolate the source contributions from detector sets, with very little cross talk, see FIG. 11.

In the signal processing system 130, the light sources 102a, 102b, 102c are modulated at three different high frequencies, respectively. In a working embodiment of the invention, the modulation frequencies were 40 kilohertz, 20 kilohertz and 10 kilohertz. Modern solid state laser diodes have very fast response times, and could be modulated at frequencies in the hundreds of megahertz range if so desired. The modulation frequencies for the three light sources 102a, 102b, 102c should be derived from a common clock oscillator 132, with conventional frequency dividers 134, 136, in order for the resulting signal processing to come out accurately without any beat frequencies.

The modulation signals from the oscillator 132 and the dividers 134, 136 are passed to driver circuits 138, 140, 142 which in turn drive the lasers or light sources 102a, 102b, 102c. The three light signals from the light sources 102a, 102b, 102c are optically mixed or added at the sensing region 124 and are converted to electric signals by each of the light sensors 110a–110c, 112a–112c, 118, 120a–120c of the optical scanner 122.

Figure 11:
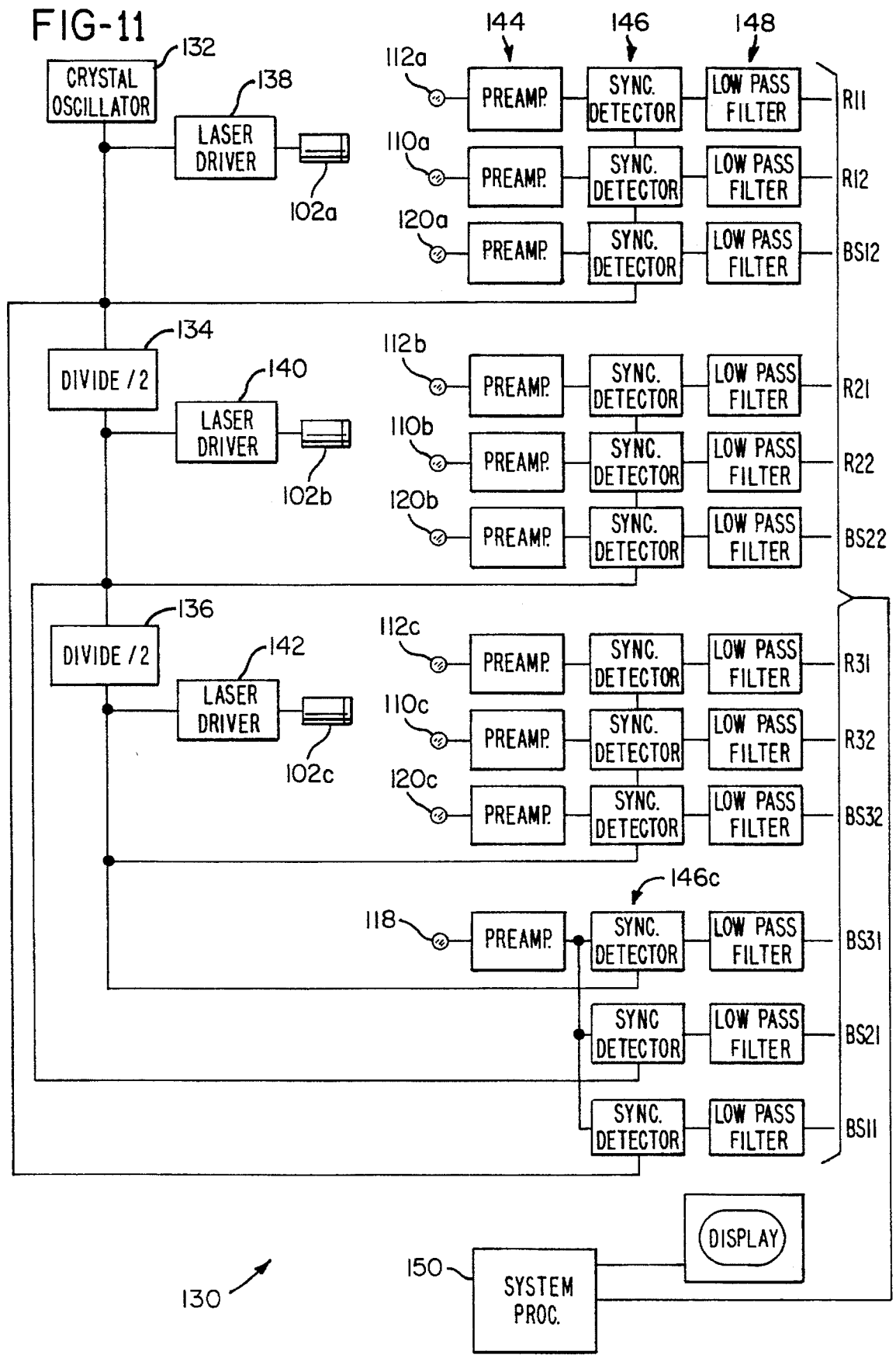
FIG. 11 is a schematic block diagram of a signal processing system for operation of the invention of the present application.

Separation of the complex signals from each of the light sensors 110a–110c, 112a–112c, 118, 120a–120c which signals are initially amplified by preamplifier circuits 144, is made by synchronous detector circuits 146 for each of the channel. The synchronous detector circuits 146 are conventional, each essentially providing a multiplier for gain of +1 or −1 dependent upon a digital control signal. The digital control signals for the synchronous detectors circuits 146 are the same as the modulation signals from the oscillator 132 and the dividers 134, 136 as shown in FIG. 11. Output signals from the central back scattered light sensor 118 are processed by a set of three synchronous detectors 146c such that signals corresponding to each of the light sources 102a, 102b, 102c can be generated.

Low pass filters 148 having a cut-off frequency of approximately 1 kilohertz in a working embodiment, remove switching components from the signals and give a pure DC signal output. By controlling the synchronous detector circuits with the modulation signals from the oscillator 132 and the dividers 134, 136, the contribution of each of the light sources 102a, 102b, 102c to the complex detector signals having components from all three of the light sources 102a, 102b, 102c can be isolated from one another. In a working embodiment, isolation for separation of the light sources 102a, 102b, 102c was approximately 40 db and 1 kilohertz bandwidth for the resulting DC signals.

In this way, the three optical paths corresponding to the light sources 102a, 102b, 102c are electrically separated from one another even though modulated light is present from all three of the light sources 102a, 102b, 102c simultaneously. The end result is three angularly separated measurements of the polar distribution function $R(\alpha)$ of fiber orientation in real time, such that the fiber orientation tilt angle $\theta$ and anisotropy a can be determined without mechanically turning either the optical scanner 122 or the web 126.

A system control 150 receives all of the output signals from the low pass filters 148 and processes them in accordance with equation (1) to derive the value of the polar distribution function for each of the three optical paths using the equations:

$$\text{at } \alpha=0°: R1^* = (R11^*R12)/(BS11^*BS12) \quad (3)$$

$$\text{at } \alpha=120°: R2^* = (R21^*R22)/(BS21^*BS22) \quad (4)$$

$$\text{at } \alpha=240°: R3^* = (R31^*R32)/(BS31^*BS32) \quad (5)$$

where R11 is the separated signal resulting from the light sensor 112a; R12 is the separated signal resulting from the light sensor 110a; R21 is the separated signal resulting from the light sensor 112b; R22 is the separated signal resulting from the light sensor 110b; R31 is the separated signal resulting from the light sensor 112c; R32 is the separated signal resulting from the light sensor 110c; BS12 is the separated signal resulting from the light sensor 120a; BS22 is the separated signal resulting from the light sensor 120b; BS32 is the separated signal resulting from the light sensor 120c; BS11 is the separated signal resulting from the light sensor 118 for the light source 102a; BS21 is the separated signal resulting from the light sensor 118 for the light source 102b; and, BS31 is the separated signal resulting from the light sensor 118 for the light source 102c.

The three resultant measurement signals at 0°, 120° and 240° (R1*, R2*, R3*) are inserted into three equations for the distribution function $R(\alpha)$, equation (2), which are accurate at the given points and the resultant three equation set with three unknowns is solved to determine fiber orientation tilt angle $\theta$ and anisotropy a.

Measurements performed by the optical scanner 122 on non-woven webs of material, such as a paper web, must be normalized in relation to reference readings taken on a fully isotropic sample, e.g., a white ceramic plate, in order to compensate for any variability between the three optical channels corresponding to the light sources 102a, 102b, 102c. Such normalization procedures are performed during a standardize cycle. While the optical scanner can be positioned at a fixed location over a web monitored, or multiple optical scanners can be provided at a number of positions across a web of material, it is preferred to mount the optical scanner on conventional scanning equipment which moves it back and forth across a web of material in the cross machine direction. For scanned configurations, the optical scanner is moved off the web, often referred to as the process, and placed over an appropriate fully isotropic sample for such calibration/normalization procedures as is common in the industry.

Additional information about the surface characteristics of the web of material being monitored is contained in the individual values of each of the raw signals going into equations 3–5. Accordingly, it is contemplated that improved mathematical processing arrangements are possible to extract much if not all of this information, in order to enhance the measurement accuracy of fiber orientation, or to further analyze the web of material, such as surface smoothness and the like.

A MD/CD ratio as well as a main axis tilt angle relative to MD can be determined after the distribution function has been solved. These may be displayed on a display device 152 as two additional profile variables derived from the optical scanner 122.

In an arrangement for on-line sensors for a paper making machine, preferably two identical optical scanners 122 will be used for top and bottom side measurements, respectively. In this way, full characterization of fiber orientation for both sides of the paper web or process can be determined, and the machine operation can be tuned or controlled to optimize the fiber orientation and reduce top to bottom fiber orientation differences in order to make a more uniform sheet with reduced tendencies for curl and other quality deficiencies.

Having thus described the invention of the present application in detail and by reference to preferred embodiments thereof, it will be apparent that modifications and variations are possible without departing from the scope of the invention defined in the appended claims.

What is claimed is:

1. A method for on-line measurement of fiber orientation in a non-woven web of material traveling in a machine direction, said method comprising the steps of:

directing light from at least three light sources toward a sensing region of said web of material, said light sources being angularly separated from one another and located within a corresponding number of incidence planes which are oriented generally perpendicular to said web of material and intersect at said sensing region for directing light toward said sensing region at incident acute angles relative to said web of material along corresponding axes within said incidence planes;

sensing light reflectively scattered from said sensing region at locations approximately diametrically opposite to each of said light sources but on either side of said incidence planes;

generating reflectance signals from sensed reflectively scattered light;

sensing light back scattered from said sensing region at locations associated with each of said light sources, said back scattered light sensing locations being generally within the incidence planes and positioned above said sensing region;

generating back scatter signals from sensed back scattered light;

combining said reflectance signals and said back scatter signals for each of said light sources to generate resultant fiber orientation signals; and computing a fiber orientation angle relative to said machine direction from said resultant fiber orientation signals.

2. A method for on-line measurement of fiber orientation in a non-woven web of material as claimed in claim 1 further comprising the step of filtering light reflectively scattered from said sensing region with polarizing filters prior to performing the step of sensing said reflectively scattered light.

3. A method for on-line measurement of fiber orientation in a non-woven web of material as claimed in claim 1 further comprising the step of modulating said at least three light sources, said step of generating reflectance signals comprises the step of demodulating sensed reflectively scattered light, and the step of generating back scatter signals comprises the step of demodulating sensed back scattered light.

4. A method for on-line measurement of fiber orientation in a non-woven web of material as claimed in claim 1 further comprising the step of computing an anisotropy characteristic for said web of material from said resultant fiber orientation signals.

5. A method for on-line measurement of fiber orientation in a non-woven web of material as claimed in claim 1 further comprising the step of angularly separating said light sources from one another by angles approximately equal to 360° divided by the number of light sources.

6. A method for on-line measurement of fiber orientation in a non-woven web of material as claimed in claim 1 wherein the step of sensing light reflectively scattered from said sensing region comprises the steps of:

sensing light a selected number of degrees to the left of each incidence plane and generally diametrically opposite to each of said light sources; and sensing light a selected number of degrees to the right of each incidence plane and generally diametrically opposite to each of said light sources.

7. A method for on-line measurement of fiber orientation in a non-woven web of material as claimed in claim 6 wherein said step of generating reflectance signals from sensed reflectively scattered light comprises the steps of:

generating a first reflectance signal from reflectively scattered light sensed a selected number of degrees to the left of each incidence plane and generally diametrically opposite to each of said light sources; and generating a second reflectance signal from reflectively scattered light sensed a selected number of degrees to the right of each incidence plane and generally diametrically opposite to each of said light sources.

8. A method for on-line measurement of fiber orientation in a non-woven web of material as claimed in claim 7 wherein the step of sensing light reflectively scattered from said sensing region is performed at reflective acute angles which are substantially the same as or less than said incident acute angles relative to said web of material.

9. A method for on-line measurement of fiber orientation in a non-woven web of material as claimed in claim 8 wherein the step of sensing light back scattered from said sensing region at locations associated with each of said light sources comprises the steps of:

sensing light substantially directly above said sensing region; and sensing light above said sensing region and a selected number of degrees toward each of said light sources generally within said incidence planes.

10. A method for on-line measurement of fiber orientation in a non-woven web of material as claimed in claim 9 wherein said step of generating back scatter signals from sensed back scattered light comprises the steps of:

generating a first back scatter signal from back scattered light sensed directly above said sensing region; and generating a second back scatter signal from back scattered light sensed above said sensing region and a selected number of degrees toward each of said light sources generally within said incidence planes.

11. A method for on-line measurement of fiber orientation in a non-woven web of material as claimed in claim 10 wherein said step of combining said reflectance signals and said back scatter signals for each of said light sources to generate resultant fiber orientation signals comprises the steps of:

multiplying said first and second reflectance signals by one another;

multiplying said first and second back scatter signals by one anther; and dividing the product of said first and second reflectance signals by the product of said first and second back scatter signals.

12. A method for on-line measurement of fiber orientation in a non-woven web of material as claimed in claim 11 wherein the steps of computing a fiber orientation angle relative to said machine direction from said resultant fiber orientation signals and computing an anisotropy characteristic for said web of material comprises the step of solving the equation:

$$R(\alpha) = K/(a + \cos(2(\alpha - \theta)))$$

for $\theta$ and a where $R(\alpha)$ is a polar distribution function of the resultant fiber orientation signals, $\alpha$ is a polar coordinate angle and K is a magnitude scaling constant, $\theta$ being a tilt angle of a main axis of orientation of the polar distribution function $R(\alpha)$ representative of the fiber orientation angle, and a is an ellipticity magnitude constant representative of anisotropy of said web.

13. An optical scanner for determining characteristics of a web of non-woven material comprising:

at least three light sources arranged to direct light toward a sensing region of said web of material at an acute angle relative to said web of material, said light sources being space from one another around said sensing region and directing light along corresponding axes;

pairs of reflective scattered light sensors corresponding in number to the number of light sources with each pair of light sensors being positioned on either side of and spaced from an incidence plane generally perpendicular to said web and including an axis along which light is directed to said sensing region by each of said light sources, said pairs of light sensors generating first sensed light signals in response to received reflectively scattered light; and at least one back scattered light sensor positioned above said sensing region of said web for generating second sensed light signals in response to received back scattered light.

14. An optical scanner for determining characteristics of a web of non-woven material as claimed in claim 13 further comprising polarizing light filters associated with said pairs of reflective scattered light sensors for filtering light reflectively scattered from said sensing region.

15. An optical scanner for determining characteristics of a web of non-woven material as claimed in claim 13 further comprising:

a modulator circuit for generating modulation signals for said light sources; and synchronous detector circuits coupled to said pairs of reflective scattered light sensors and said back scattered light sensor and driven by said modulation signals for extracting source signals corresponding to said light sources from said first and second sensed light signals.

16. An optical scanner for determining characteristics of a web of non-woven material as claimed in claim 15 wherein said modulator circuit comprises:

a clock for generating a first signal having a substantially fixed frequency;

a first divider circuit for dividing said first signal by 2 to generate a second signal having a frequency substantially half of said first signal; and a second divider circuit for dividing said second signal by 2 to generate a third signal having a frequency substantially half of said second signal, said first, second and third signals serving as said modulation signals.

17. An optical scanner for determining characteristics of a web of non-woven material as claimed in claim 16 wherein said first frequency is approximately 40 kilohertz, said second frequency is approximately 20 kilohertz and said third frequency is approximately 10 kilohertz.

18. An optical scanner for determining characteristics of a web of non-woven material as claimed in claim 15 further comprising low pass filters for converting said source signals to reflectance signals representative of said sensed reflectively scattered light and back scatter signals representative of said sensed back scattered light.

19. An optical scanner for determining characteristics of a web of non-woven material as claimed in claim 18 wherein said low pass filters pass frequencies equal to and below approximately 1 kilohertz.

20. A method for generating signals representative of fiber orientation in a non-woven web of material comprising the steps of:

directing light from a light source toward a sensing region of said web of material, said light being directed at said sensing region at an acute incident angle relative to said web of material and being in an incidence plane which is oriented generally perpendicular to said web of material and intersecting said sensing region;

sensing light reflectively scattered from said sensing region at a location approximately diametrically opposite to said light source but only on either side of said incidence plane, not on said incidence plane, said step of sensing reflectively scattered light being performed at a reflective acute angle relative to said web of material which is at least somewhat less than the acute incident angle of light directed from said light source; and generating signals representative of fiber orientation from sensed reflectively scattered light.

21. A method for generating signals representative of fiber orientation in a non-woven web of material as claimed in claim 20 further comprising the steps of:

sensing light back scattered from said sensing region at a location generally within the incidence plane and positioned above said sensing region; and generating signals representative of fiber orientation from sensed back scattered light.

22. A method for generating signals representative of fiber orientation in a non-woven web of material as claimed in claim 21 wherein said step of generating signals representative of fiber orientation from sensed reflectively scattered light comprises the step of generating reflectance signals, said step of generating signals representative of fiber orientation from sensed back scattered light comprises the step of generating back scatter signals and said method further comprises the step of combining said reflectance signals and said back scatter signals for said light source to generate resultant fiber orientation signals.

* * * * *